United States Patent
Gohndrone

(10) Patent No.: US 9,908,903 B2
(45) Date of Patent: Mar. 6, 2018

(54) METHOD OF PRODUCING ORGANOHALOSILANES

(71) Applicant: Dow Corning Corporation, Midland, MI (US)

(72) Inventor: John Michael Gohndrone, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 15/527,558

(22) PCT Filed: Feb. 3, 2016

(86) PCT No.: PCT/US2016/016349
§ 371 (c)(1),
(2) Date: May 17, 2017

(87) PCT Pub. No.: WO2016/126808
PCT Pub. Date: Aug. 11, 2016

(65) Prior Publication Data
US 2017/0369514 A1    Dec. 28, 2017

Related U.S. Application Data

(60) Provisional application No. 62/112,871, filed on Feb. 6, 2015.

(51) Int. Cl.
| | |
|---|---|
| *C07F 7/14* | (2006.01) |
| *B01J 21/04* | (2006.01) |
| *B01J 21/06* | (2006.01) |
| *B01J 37/24* | (2006.01) |
| *B01J 37/08* | (2006.01) |

(52) U.S. Cl.
CPC ............ *C07F 7/14* (2013.01); *B01J 21/04* (2013.01); *B01J 21/066* (2013.01); *B01J 37/08* (2013.01); *B01J 37/24* (2013.01)

(58) Field of Classification Search
None
See application file for complete search history.

(56) References Cited

U.S. PATENT DOCUMENTS

| | | |
|---|---|---|
| 2,775,606 A | 12/1956 | Wagner et al. |
| 4,543,347 A | 9/1985 | Heyward et al. |
| 4,889,838 A | 12/1989 | Lewis et al. |
| 5,136,070 A | 8/1992 | Bank |
| 5,220,069 A | 6/1993 | King et al. |
| 6,686,492 B2 | 2/2004 | Nguyen |
| 6,747,168 B2 | 6/2004 | Chaturvedi et al. |
| 8,492,592 B2 | 7/2013 | King et al. |
| 8,962,877 B2 | 2/2015 | Kohane et al. |
| 9,296,765 B2 | 3/2016 | Coppernoll et al. |
| 2011/0132744 A1 | 6/2011 | Auner et al. |
| 2013/0072710 A1 | 3/2013 | Brazdil et al. |

OTHER PUBLICATIONS

A.J. Barry, J.W. Gilkey, and D.E. Hook, "Preparation of Arylhalosilanes", Advances in Chemistry vol. 51(2), Feb. 1959.
A. Wright, The Role of Boron Trichloride in the Synthesis of Phenyltrichlorosilane from Benzene and Trichlorosilane, J.Org. Chem. vol. 145, pp. 307-314, (1978).

*Primary Examiner* — Clinton A Brooks
(74) *Attorney, Agent, or Firm* — Catherine U. Brown

(57) ABSTRACT

A method for producing an organohalosilane, the method comprising: reacting an organic compound comprising a halogen-substituted or unsubstituted aromatic compound with a hydridohalosilane mixture comprising at least two different hydridohalosilanes of formula (I) $R_nSiH_mX_{4-m-n}$, where each R is independently $C_1$-$C_{14}$ hydrocarbyl or $C_1$-$C_{14}$ hologen-substituted hydrocarbyl, X is fluoro, chloro, bromo, or iodo, n is 0, 1, or 2, m is 1, 2, or 3 and m+n is 1, 2, or 3, in the presence of a catalyst comprising one or more of the elements Sc, Y, Ti, Zr, Hf, Nb, B, Al, Ga, In, C, Si, Ge, Sn, or Pb, at a temperature greater than 100° C., and at a pressure of at least 690 kPa, to produce a crude reaction product comprising the organohalosilane, provided that when the at least two different hydridohalosilane comprise a hydridohalosilane of formula (I) where n=0 and m=1 and a hydridohalosilane of formula (I) where n=0 and m=2, the catalyst is a heterogeneous catalyst comprising an oxide of one or more of the elements Sc, Y, Ti, Zr, Hf, B, Al, Ga, In, C, Si, Ge, Sn, or Pb.

16 Claims, No Drawings

METHOD OF PRODUCING ORGANOHALOSILANES

This application is a U.S. national stage filing under 35 U.S.C. § 371 of PCT Application No. PCT/US16/016349 filed on 3 Feb. 2016, currently pending, which claims the benefit of U.S. Provisional Patent Application No. 62/112,871 filed 6 Feb. 2015 under 35 U.S.C. § 119 (e). PCT Application No. PCT/US16/016349 and U.S. Provisional Patent Application No. 62/112,871 are hereby incorporated by reference.

The present invention relates to methods of producing organohalosilanes and, more particularly, to methods comprising reacting an organic compound comprising a halogen-substituted or unsubstituted aromatic compound with at least two different hydridohalosilanes in the presence of a catalyst comprising one or more of the elements Sc, Y, Ti, Zr, Hf, Nb, B, Al, Ga, In, C, Si, Ge, Sn, or Pb.

Processes for making aromatic organohalosilanes through reactions with hydridohalosilanes are known. In one such process, benzenoid and alkyl-substituted benzenoid hydrocarbons have been reacted with trichlorosilane in the presence of a soluble boron halide catalyst at a temperature above 230° C. and under pressure to produce, for example, phenyltrichlorosilane. Other variations of this process have also been described using similar reaction conditions. For example, polyhalomonohydridosilanes such as those containing one hydrogen atom and two halogen atoms bonded to the silicon atom and the remaining valence on the silicon being taken up by a monovalent hydrocarbon radical have been reacted with benzenoid hydrocarbons using a boron halide catalyst. In another example, silicon-borate catalysts have been used in the reaction between trichlorosilane and naphthalene or benzenoid hydrocarbons free of any aliphatic unsaturation to make aromatic chlorosilanes. In yet another example, mixtures of dichlorosilane and trichlorosilane have been reacted with benzene in the presence of a soluble Lewis acid metal halide and a metal hydride complex to favor production of phenyldichlorosilane over phenyltrichlorosilane or diphenyldichlorosilane. In still another variation, an aromatic halohydrocarbon was reacted with methyldichlorosilane in the presence of soluble boron trichloride or soluble aluminum chloride to produce an organodichlorosilyl derivative of the aromatic halohydrocarbon without displacement of the halogen from the aromatic ring structure.

Organohalosilanes have also been made by the reaction an olefin with a hydridohalosilane in the present of a supported heterogeneous transition metal catalyst. For example, hydridohalosilanes have been reacted with olefins in the presence of supported platinum catalysts.

Existing processes for producing organohalosilanes by the reaction of an organic compound, such as an aromatic compound, with a hydridohalosilane in the presence of a catalyst are deficient in some respects. For example, some catalysts used in the processes described above with aromatic organic compounds are homogeneous catalysts, which are difficult to remove from the crude product. The presence of catalyst in the crude product can cause issues in the recovery of the product. For example, the product is typically recovered through distillation, but the homogeneous or soluble catalysts described above can catalyze rearrangement reactions in the distillation column reducing yields and increasing unwanted byproducts. To avoid these catalyzed rearrangements, the catalyst can be deactivated before distillation through the addition of a catalyst poison; however, addition of a poison increases the cost and complexity of the process, introduces an unwanted material, and renders the catalyst unusable and unrecyclable.

Hydrosilation reactions involving reaction of a hydridohalosilane in the presence of a transition metal catalyst are limited to olefins and are not effective for the reaction of Si—H (hydridochlorosilanes) across aryl or alkyl C—H bonds.

Finally, in addition to the deficiencies described above related to the separation of catalyst from reaction products and catalyst effectiveness across aryl and alkyl C—H bonds, there also exist needs related to process economics and safety such as improving reaction yields, catalyst reuse, reducing reaction pressures, and reducing reaction temperatures.

BRIEF SUMMARY OF THE INVENTION

The invention is directed to a method for producing an organohalosilane, the method comprising: reacting an organic compound comprising a halogen-substituted or unsubstituted aromatic compound with a hydridohalosilane mixture comprising at least two different hydridohalosilanes of formula (I) $R_nSiH_mX_{4-m-n}$, where each R is independently $C_1$-$C_{14}$ hydrocarbyl or $C_1$-$C_{14}$ hologen-substituted hydrocarbyl, X is fluoro, chloro, bromo, or iodo, n is 0, 1, or 2, m is 1, 2, or 3 and m+n is 1, 2, or 3, in the presence of a catalyst comprising one or more of the elements Sc, Y, Ti, Zr, Hf, Nb, B, Al, Ga, In, C, Si, Ge, Sn, or Pb, at a temperature greater than 100° C., and at a pressure of at least 690 kPa, to produce a crude reaction product comprising the organohalosilane, provided that when the at least two different hydridohalosilane comprise a hydridohalosilane of formula (I) where n=0 and m=1 and a hydridohalosilane of formula (I) where n=0 and m=2, the catalyst is a heterogeneous catalyst comprising an oxide of one or more of the elements Sc, Y, Ti, Zr, Hf, B, Al, Ga, In, C, Si, Ge, Sn, or Pb.

Embodiments of the method of the invention produce organohalosilanes in better yields and at lower temperature and pressure than with previously known processes. Further, embodiments of the invention allow for easy separation of the catalyst from the crude reaction product, decreasing catalysis of unwanted reactions during additional processing and increasing product purity.

The organohalosilane products of the present method are used as precursors to make many different commercial products including arylsiloxanes which also have many commercial uses.

DETAILED DESCRIPTION OF THE INVENTION

The Brief Summary and Abstract are incorporated here by reference. The invention embodiments, uses and advantages summarized above are further described below.

Aspects of the invention are described herein using various common conventions. For example, all states of matter are determined at 25° C. and 101.3 kPa unless indicated otherwise. All % are by weight unless otherwise noted or indicated. All % values are, unless otherwise noted, based on total amount of all ingredients used to synthesize or make the composition, which adds up to 100%. Any Markush group comprising a genus and subgenus therein includes the subgenus in the genus, e.g., in "R is hydrocarbyl or alkenyl," R may be alkenyl, alternatively R may be hydrocarbyl, which includes, among other subgenuses, alkenyl. For U.S. practice, all U.S. patent application publications and patents referenced herein, or a portion thereof if only the portion is referenced, are hereby incorporated herein by reference to the extent that incorporated subject matter does not conflict with the present description, which would control in any such conflict.

Aspects of the invention are described herein using various patent terms. For example, "alternatively" indicates a different and distinct embodiment. "Comparative" as used in comparative example, comparative process or comparative method means a non-invention experiment and should not be interpreted as prior art. "Comprises" and its variants (comprising, comprised of) are open ended. "Consists of" and its variants (consisting of) are closed ended. "Contacting" means bringing into physical contact. "May" confers a choice, not an imperative. "Optionally" means is absent, alternatively is present.

A method for producing an organohalosilane, the method comprising: reacting an organic compound comprising a halogen-substituted or unsubstituted aromatic compound with a hydridohalosilane mixture comprising at least two different hydridohalosilanes of formula (I) $R_nSiH_mX_{4-m-n}$, where each R is independently $C_1$-$C_{14}$ hydrocarbyl or $C_1$-$C_{14}$ hologen-substituted hydrocarbyl, X is fluoro, chloro, bromo, or iodo, n is 0, 1, or 2, m is 1, 2, or 3 and m+n is 1, 2, or 3, in the presence of a catalyst comprising one or more of the elements Sc, Y, Ti, Zr, Hf, Nb, B, Al, Ga, In, C, Si, Ge, Sn, or Pb, at a temperature greater than 100° C., and at a pressure of at least 690 kPa, to produce a crude reaction product comprising the organohalosilane, provided that when the at least two different hydridohalosilane comprise a hydridohalosilane of formula (I) where n=0 and m=1 and a hydridohalosilane of formula (I) where n=0 and m=2, the catalyst is a heterogeneous catalyst comprising an oxide of one or more of the elements Sc, Y, Ti, Zr, Hf, B, Al, Ga, In, C, Si, Ge, Sn, or Pb.

The organic compound comprises a halogen-substituted or unsubstituted aromatic compound. The organic compound has from 6 to 14 carbon atoms; alternative from 6 to 10 carbon atoms; alternatively from 6 to 8 carbon atoms; alternatively 6 carbon atoms. Organic compounds can have cyclic or polycyclic structure, such as fused, bridged or spiro structure.

Examples of unsubstituted aromatic compounds include, but are not limited to, benzene, toluene, 1,3-dimethylbenzene, 1,4-dimethylbenzene, 1-phenylethene, 1-phenyl-1-propene, naphthalene, and 1,1-diphenylethene. Examples of halogen-substituted aromatic compounds include, but are not limited to, the aromatic compounds exemplified above with a fluoro, chloro, bromo, or iodo group, alternatively a chloro group substituted for one of the hydrogen atoms of the aromatic compound, such as chlorobenzene or dichlorobenzene.

The hydridohalosilane mixture comprises at least two different hydridohalosilanes of formula (I) $R_nSiH_mX_{4-m-n}$, where each R is independently $C_1$-$C_{14}$ hydrocarbyl or $C_1$-$C_{14}$ hologen-substituted hydrocarbyl, X is fluoro, chloro, bromo, or iodo, alternatively X is chloro, n is 0, 1, or 2, alternatively n is 0 or 1, m is 1, 2, or 3, alternatively m is 1 or 2, and m+n=1, 2, or 3.

The phrase "at least two different hydridohalosilanes of formula (I)" means that the hydridohalosilane mixture comprises two or more hydridohalosilanes each having chemical structures according to formula (I) but different structures from each other.

The hydrocarbyl groups represented by R in formula (I) typically have from 1 to 14 carbon atoms, alternatively from 1 to 10 carbon atoms, alternatively from 1 to 4 carbon atoms, alternatively 1 or 2 carbon atoms; alternatively 1 carbon atom. Acyclic hydrocarbyl groups containing at least 3 carbon atoms can have a branched or unbranched structure. Examples of $C_1$-$C_{14}$ hydrocarbyl groups represented by R include, but are not limited to, alkyl, such as methyl, ethyl, propyl, 1-methylethyl, butyl, 1-methylpropyl, 2-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, decyl, undecyl, dodecyl, tridecyl, and tetradecyl; cycloalkyl, such as cyclopentyl, cyclohexyl, and methylcyclohexyl; aryl, such as phenyl and naphthyl; alkaryl, such as tolyl and xylyl; aralkyl such as benzyl and phenylethyl.

Examples of the hydridohalosilanes according to formula (I) of the invention include, but are not limited to, monochlorosilane, dichlorosilane, trichlorosilane, methylchlorosilane, methyldichlorosilane, dimethylchlorosilane, ethylchlorosilane, ethyldichlorosilane, diethylchlorosilane, propylchlorosilane, propyldichlorosilane, dipropylchlorosilane, butylchlorosilane, butyldichlorosilane, dibutylchlorosilane, pentylchlorosilane, pentyldichlorosilane, dipentylchlorosilane, hexylchlorosilane, hexyldichlorosilane, dihexylchlorosilane, octylchlorosilane, octyldichlorosilane, dioctylchlorosilane, decylchlorosilane, decyldichlorosilane, didecylchlorosilane, tetradecylchlorosilane, tetradecyldichlorosilane, ditetradecylchlorosilane, phenylchlorosilane, phenyldichlorosilane, diphenylchlorosilane, benzylchlorosilane, benzyldichlorosilane, dibenzylchlorosilane. Methods of making the hydridohalosilanes of the invention are known in the art.

Examples of the hydridohalosilane mixture include, but are not limited to, a mixture comprising at least two of the hydridohalosilanes exemplified above for the hydridohalosilanes according to formula (I), alternatively, comprising dichloro(methyl)silane and dichlorosilane, alternatively comprising dichloro(methyl)silane and trichlorosilane, alternatively comprising dichloro(methyl)silane and monochlorosilane.

There is no particular ratio of hydridohalosilanes in the hydridohalosilane mixture relative to one another; alternatively the hydridohalosilane mixture comprises 5 to 95% (mol/mol), alternatively 5-25% (mol/mol), alternatively 5-15% (mol/mol), based on the moles of all hydridohalosilanes, of dichlorosilane; alternatively the hydridohalosilane mixture comprises dichlorosilane and trichlorosilane, where the hydridohalosilane mixture comprises 5 to 95% (mol/mol), alternatively 5-25% (mol/mol), alternatively 5-15% (mol/mol), based on the moles dichlorosilane and trichlorosilane, of dichlorosilane; alternatively the hydridohalosilane mixture comprises dichlorosilane and dichloro(methyl) silane, where the hydridohalosilane mixture comprises from 5 to 95% (mol/mol), alternatively 5-25% (mol/mol), alternatively 5-10% (mol/mol), based on the moles dichlorosilane and dichloro(methyl)silane, of dichlorosilane.

The inclusion of at least two hydridohalosilanes in the reaction of the invention is believed to enhance the yield of and selectivity for the organohalosilane product. In addition, the use of the at least two hydridohalosilanes is believed to allow the production of the organohalosilane at lower temperature than if only one hydridohalosilane is used.

The catalyst comprises one or more of the elements Sc, Y, Ti, Zr, Hf, Nb, B, Al, Ga, In, C, Si, Ge, Sn, or Pb, provided that when the at least two different hydridohalosilane comprise a hydridohalosilane of formula (I) where n=0 and m=1 and a hydridohalosilane of formula (I) where n=0 and m=2, the catalyst is a heterogeneous catalyst comprising an oxide of one or more of the elements Sc, Y, Ti, Zr, Hf, B, Al, Ga, In, C, Si, Ge, Sn, or Pb In one embodiment, the catalyst has the formula $B_aZ_b$, $NbZ_5$, or $AlZ_3$, where Z is H, R, where R is as defined above in reference to formula (I), or halo, a is 1 or 2, and b is 3 or 6; alternatively Z is H, R, F, Cl, Br, or I, a is 1 or 2, and b is 3 or 6, alternatively Z is H, R, or Cl, a is 1 or 2, and b is 3 or 6, alternatively Z is H, phenyl, methyl, or Cl, a is 1 or 2, and b is 3 or 6. Examples of the catalyst having the formula $B_aZ_b$, $NbZ_5$, or $AlZ_3$ include $PhBCl_2 Ph_3B$, $B_2H_6$, $NbCl_5$, $AlCl_3$, $BCl_3$, all of which may be purchased.

As used herein in reference to the catalyst, "heterogeneous" means that the catalyst and the reactants form two phases, such as, but not limited to, a solid phase and a liquid phase; "soluble" means that the catalyst and the reactants form one phase; and "oxide" means a compound having at least one oxygen and at least one other element in its chemical formula.

In one embodiment, the catalyst comprises a heterogeneous catalyst which comprises an oxide of one or more of the elements Sc, Y, Ti, Zr, Hf, B, Al, Ga, In, C, Si, Ge, Sn, or Pb, alternatively one or more of Sc, Y, Ti, Zr, B, Al, Si, or Ge, alternatively an oxide of two or more of Sc, Y, Ti, Zr, B, Al, Si, or Ge, alternatively alumina, zirconium dioxide, an oxide comprising Al and one of the elements B, Zr, Ti, or Si, or an oxide comprising Zr and one of the elements B, Ti, or Si, alternatively γ-alumina or zirconium dioxide, alternatively an oxide comprising Al and B, an oxide comprising Al and Si, or an oxide comprising Zr and B, alternatively an oxide comprising Al and B or an oxide comprising Zr and B, alternatively γ-alumina, alternatively an oxide of formula $Al_9B_2O_{15}$ or $Al_4B_2O_9$. It will be apparent to one skilled in the art that all of the oxides of the invention contain oxygen. The oxygen atoms are present in the oxide in sufficient quantity to satisfy the valence requirements of the other atoms unless otherwise noted.

In one embodiment, the heterogeneous catalyst is an oxide of formula $M^1_a M^2_b M^3_c M^4_d O_x$, where $M^1$, $M^2$, $M^3$ and $M^4$ are each independently Sc, Y, Ti, Zr, Hf, B, Al, Ga, In, C, Si, Ge, Sn, or Pb, a, b, c, and d are each independently from 0 to 1.00, and a+b+c+d>0, alternatively $M^1$, $M^2$ and $M^3$ are each independently Sc, Y, Ti, Zr, B, Al, Si, or Ge, a is from 0 to 1.00, b is from 0 to 1.00, c is from 0 to 1.00, d=0, and a+b+c>0, alternatively $M^1$ is Ti, Zr, B, or Al, $M^2$ is Ti, Zr, B, or Al, $M^3$ is Sc or Y, $M^4$ is Si or Ge, a is from 0 to 1.00, b is from 0 to 1.00, c is from 0 to 0.10, d is from 0 to 0.50, a+b+c+d>0, if a=0 then b>0 and when b=0 then a>0, alternatively $M^1$ is Al, $M^2$ is Zr, $M^3$ is B, Ti, or Si, a is from 0 to 1.00, alternatively a=0, b is from 0 to 1.00, alternatively b=0, c is from 0 to 0.50, alternatively c is from 0 to 0.30, d=0, a+b+c>0, and if a=0 then b>0 and if b=0 then a>0, alternatively $M^1$ is Zr or Al, a is >0 to 1, and b, c, and d=0, x is the number of oxygen atoms in the oxide and is sufficient to satisfy the valence of the other atoms in the oxide, alternatively x is from >0 to 1.00. The letters a, b, c, d, and x represent the gram-atom ratio of the elements present in the oxide. $M^{1-4}$ are all different in the embodiments described above.

Examples of the heterogeneous catalyst include, but are not limited to, alumina in any form, such as eta-alumina, nanosheets, α-alumina, and γ-alumina; zirconium dioxide, $ZrO_2$, in any form such as monoclinic, tetragonal, or cubic; composite oxides comprising the elements of Al and one of the elements Ti, Zr, or B, alternatively one of the elements B, Zr, Ti, or Si, including, but not limited to, oxides having the formula $Al_9B_2O_{15}$ and $Al_4B_2O_9$; and composite oxides of the elements Zr and one of the elements Ti, Al, or B, alternatively one of the elements Ti, B, or Si. Alumina and zirconium dioxide are known the art and available commercially in their different forms. For example, γ-alumina may be purchased from Clariant International, Ltd., of Munich, Germany.

The composition of the heterogeneous catalyst may be determined by methods known in the art. For example, the composition may be determined by X-ray crystallography, electron microscopy, elemental analysis, mass spectroscopy, electrochemical methods, or a combination of these methods.

The heterogeneous catalyst may also comprise a binder or carrier. For example, the heterogeneous catalyst may comprise a graphite or aluminum stearate binder. Graphite and aluminum stearate are available commercially. Binders are typically used to control the shape of the heterogeneous catalyst.

When the heterogeneous catalyst comprises a binder, the heterogeneous catalyst typically comprises less than 25% (w/w), alternatively less than 10% (w/w) of binder. The heterogeneous catalysts comprising binder are commercially available from Clariant International, Ltd.

The heterogeneous catalyst may be in any shape. For example, the heterogeneous catalyst may be in powder, granule, pellet or any extrudate form.

The heterogeneous catalyst may be an oxide of a single element, a physical mixture of two or more oxides of different elements, or a composite oxide. As used herein, "composite oxide" is intended to mean, but is not limited to, an oxide comprising a combination with two or more elements and includes crystallite composites; composites coated, doped, attached, loaded, or supported with other active components; matrix materials; hybrid composites comprising a matrix material in which one or more of the metal oxide phases is dispersed; and hierarchical porous composites, having pore systems such as micropores, mesopores and macropores.

The catalyst may be made by methods known in the art or purchased commercially from, for example, Sigma-Aldrich or Clariant International, Ltd., of Munich, Germany. When the heterogeneous catalyst comprises a binder and/or two or more metal oxides, the metal oxide may be physically mixed with the binder and any other metal oxides by extrusion or other preparation and mixing techniques known in the art. Composite oxides comprised by the heterogeneous catalyst may be made by methods known in the art, such as an in situ sol-gel hydrolysis or co-precipitation followed by calcination, core-shell growth, intergrowth, overgrowth, or co-crystallization. For example, a composite oxide comprising B and Al may be made according to the procedure described in the examples, where ground $H_3BO_3$, glycerol, ground $Al(NO_3)_3 \cdot 9H_2O$ and de-ionized water are combined and heated to 90° C. for 2 hours followed by heating at 150° C. then 400° C. to form the composite.

The process of the invention may be carried out in any reactor suitable for conducting reactions of the type of the invention. For example, the process may be carried out in a batch reactor such as a sealed tube reactor or in a continuous reactor such as a packed column. Reactors such as tube reactors and packed columns are available commercially. For example, tube reactors may be purchased from the Parr Instrument Company, having offices in Moline, Ill. Other manufactures of suitable pressure reactors include High Pressure Equipment Company of Erie, Pa., Parker Autoclave Engineers of Erie Pa., Büchi AG of Uster, Switzerland, Berghof of Eningen, Germany, and Zeyon, Inc., of Erie, Pa.

The process of the invention is carried out at a temperature of at least 100° C., alternative from 100° C. to 300° C., alternatively from 150° C. to 275° C., alternatively from 195° C. to 255° C. At temperatures much above 300° C., the heterogeneous metal oxide catalysts may become unstable and ineffective as catalysts.

The process of the invention may be carried out at a pressure of at least 690 kPa, alternatively at least 3500; alternatively from 4000 to 11000 kPa; alternatively from 4000 to 6000 kPa.

The process of the invention may be carried out continuously or may conducted using in a batch process. Alternatively, the process is conducted continuously with the heterogeneous catalyst by flowing the organic compound and the hydridohalosilane mixture over the heterogeneous catalyst. As used herein, "continuously" means that a stream of organic compound and hydridohalosilanes are constantly fed to the reactor containing the heterogeneous catalyst while the organohalosilane product, unreacted organic compound and hydridohalosilane, and any byproducts are removed. When the catalyst is a homogeneous catalyst, the process of the invention may be carried out according to methods known in the art for similar reactions comprising only one hydridohalosilane and known homogeneous catalysts.

When the process of the invention is carried out continuously with the heterogeneous catalyst, the contact time is between 0.001 s to 100 minute; alternatively from 1 s to 50 minutes; alternatively from 10 to 30 minutes. As used herein "contact time" is intended to mean the time for one reactor volume of the reactants (i.e., organic compound and hydridohalosilane mixture) to pass through the reactor charged with catalyst.

The catalyst is typically in a catalytic effective amount with respect to the organic compound and the hydridohalosilane. A catalytic effective amount is an amount sufficient to catalyze the reaction between the organic compound and the hydridohalosilane. For example, a catalytic effective amount of heterogeneous catalyst is at least 0.01 mg catalyst/cm$^3$ of reactor volume; alternatively at least 0.5 mg catalyst/cm$^3$ of reactor volume; alternatively from 1 to 10,000 mg catalyst/cm$^3$ of reactor volume. Alternatively a catalytic effective amount is from 0.01 to 50 mol %, alternatively from 0.1 to 15 mol %, alternatively from 0.1 to 5 mol %, based on the weight of all reagents in the reactor. One skilled in the art would know how to determine the correct amount of catalysts depending upon whether using a heterogeneous, homogeneous, or combination of homogeneous and heterogeneous catalysts; whether a batch or continuous process is used; and the type of reactor used. For example, in a continuous reaction in a column, the reactor may be filled with heterogeneous catalyst and the reactants passed between the voids in the catalyst.

There is no required order of addition for the reaction when a batch process is used. In a continuous process the hydridohalosilane and the organic compound must be contacted together in the presence of the heterogeneous catalyst. For example, the organic compound and the hydridohalosilane are mixed and flowed together over the heterogeneous catalyst in a continuous reaction. With a homogenous catalyst is used, the reactions are carried out according to known orders of addition.

The molar ratio of organic compound to hydridohalosilanes is from 0.5 to 10; alternatively from 0.5 to 4; alternatively from 1 to 4.

The heterogeneous catalyst may be treated with an acid to remove moisture and reduce surface hydroxyl groups prior to the reacting of the organic compound and the hydridohalosilanes. The acid may be any acid that will reduce the hydroxyl on the surface and remove moisture. In one embodiment, the catalyst is treated with acid prior to the reacting taking place in the process.

Examples of acids that may be used to treat the heterogeneous catalyst include, but are not limited to, halosilanes, mixtures of halosilanes, hydrogen chloride and mixtures of hydrogen chloride and halosilanes. Alternatively, the heterogeneous catalyst is treated with HCl. Hydrogen chloride and halosilanes are available commercially. Chlorosilanes and mixtures of chlorosilanes may be produced or purchased commercially. Methods of producing halosilanes and mixtures of halosilanes are known in the art. The definition of halosilanes as used herein is intended to include halosilanes alone, alkylhalosilanes alone, or combinations of halosilanes and alkylhalosilanes.

The heterogeneous catalyst may be treated with the acid by means known in the art for treating a catalyst with HCl or a halosilane. For example, the heterogeneous catalyst may be treated by flowing hydrogen chloride, halosilanes, a mixture of halosilanes, or a mixture of HCl and a halosilane over the heterogeneous catalyst at between 60° C. and 300° C., alternatively between 150° C. and 75° C. Alternatively, the heterogeneous catalyst is treated with the hydridohalosilane mixture described above for reacting with the organic compound by starting the flow of the hydridohalosilane mixture in a continuous process prior to the flow of the organic compound at a temperature from 100° C. to 300° C., alternatively from 150° C. to 275° C.

The organohalosilane produced according to the invention may be recovered after the reaction from the crude reaction product. As used herein, "crude reaction product" means the product of the reaction between the organic compound and the hydridohalosilane mixture before any steps are taken to recover the organhalosilane produced. Example of methods of recovering the organohalosilane include, but are not limited to, filtration and distillation. One skilled in the art would know how to filter and distill the oganohalosilane produced according to the invention.

The method of the invention produces a crude reaction product comprising the organohalosilanes. The organohalosilane produced according to the invention has the formula $R'_e R_f SiH_g X_{4-e-f-g}$, where R and X are as defined above for the hydridohalosilane, each R' is independently $C_1$-$C_{14}$ hydrocarbyl, subscript e is 1 or 2, subscript f is 0, 1, or 2, subscript g is 0, 1, or 2, and the sum of the subscripts e+f+g=1, 2 or 3.

The hydrocarbyl groups represented by R' typically have from 1 to 14 carbon atoms, alternatively from 1 to 10 carbon atoms, alternatively from 1 to 6 carbon atoms, alternatively 6 carbon atoms. Examples of the hydrocarbyl groups are those formed by the removal of a hydrogen atom from the organic compound. Acyclic hydrocarbyl groups containing at least three carbon atoms can have a branched or unbranched structure. Examples of hydrocarbyl groups include, but are not limited to, alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, decyl, undecyl, dodecyl, tridecyl, and tetradecyl; cycloalkyl, such as cyclopentyl, cyclohexyl, and methylcyclohexyl; aryl, such as phenyl, and naphthyl; alkaryl, such as tolyl, and xylyl; aralkyl such as benzyl and phenylethyl; aralkenyl, such as styryl and cinnamyl. The hydrocarbyl groups may be substituted with halo groups. Examples of substituted hydrocarbyl groups represented by R include those defined above for R with a halogen, such as chlorine, bromine, or iodine substituted for a hydrogen atom of the hydrocarbyl group.

Examples of organohalosilanes produced according to the invention include, but are not limited to, trichloro(methyl)silane, trichloro(ethyl)silane, trichloro(propyl)silane, trichloro(butyl)silane, trichloro(pentyl)silane, trichloro(octyl)silane, trichloro(tetradodecyl)silane, trichloro(chloromethyl)silane, trichloro-(2-chloroethyl)silane, trichloro-(3-chloropropyl)silane, trichloro-(4-chlorobutyl)silane, trichloro(cyclohexyl)silane, trichloro-(3-chlorocyclohexyl)silane, trichloro(vinyl)silane, allyltrichlorosilane, 3-butenetrichlorosilane, trichloro(4-pentene)silane, trichloro(7-octene)silane, trichloro(13-tetradodecene)silane, trichloro-(2-chloroethene)silane, trichloro-(3-chloropropene)silane, trichloro-(4-chlorobut-3-ene)silane, trichloro(1-cyclohexene)silane, trichloro-(3-methylcyclohex-1-ene)silane, trichloro-(3-chlorocyclohex-1-ene)silane, trichloro(phenyl)silane, trichloro(naphthyl)silane, trichloro-(3-chlorophenyl)silane, trichloro-(4-chloronaphthyl)silane, trichloro(tolyl)silane, xylyltrichlorosilane, dichloro(dimethyl)silane, dichloro(ethyl)methylsilane, dichloro(methyl)propylsilane, dichloro(butyl)methylsilane, dichloro(methyl)pentylsilane, dichloro(methyl)octylsilane, dichloro(tetradecyl)methylsilane, dichlorochloromethyl(methyl)silane, 2-dichloro(chloroethyl)methylsilane, dichloro(3-chloropropyl)methylsilane, 4-dichloro(chlorobutyl)methylsilane, dichloro(cyclohexyl)methylsilane, dichloro(3-chlorocyclohexyl)methylsilane, dichloro(vinyl)methylsilane, allyl(dichloro)methylsilane, 3-butene(dichloro)methylsilane, dichloro(methyl)-4-pentenesilane, dichloro(methyl)-7-octenesilane, dichloro(13-tetradodecene)methylsilane, dichloro-(2-chloroethene)methylsilane, dichloro-(3-chloropropene)methylsilane, dichloro-(4-chlorobut-3-ene)methylsilane, dichloro(1-cyclohexene)methylsilane, dichloro-(3-methylcyclohex-1-ene)methylsilane, dichloro-(3-chlorocyclohex-1-ene)methylsilane, dichloro(phenyl)methylsilane, dichloro(naphthyl)methylsilane, dichloro(xylyl)methylsilane dichloro(m-chlorophenyl)methylsilane, dichloro(4-chloronaphthyl)methylsilane, dichloro(chlorotolyl)methylsilane, dichloro(chloroxylyl)methylsilane, diethyldichlorosilane, dipropyldichlorosilane, dibutyldichlorosilane, dipentyldichlorosilane, dichloromethyldichlorosilane, bis-(2-chloroethyl)dichlorosilane, bis-(3-chloropropyl)dichlorosilane, dihexyldichlorosilane, dicyclohexyldichlorosilane, bis-(3-chlorocyclohexyl)dichlorosilane, dichloro(divinyl)silane, diallyl(dichloro)silane, bis-3-butenedichlorosilane, diphenyldichlorosilane, dinaphthyldichlorosilane, bis-(3-chlorophenyl)dichlorosilanes, bis-(4-chloronaphthyl)dichlorosilanes, chloro(trimethyl)silane, chloro(triethyl)silane, chloro(tripropyl)silane, chloro(tributyl)silane, chloro(tripentyl)silane, chloro(trihexyl)silane, chloro(triheptyl)silane, chloro(trioctyl)silane, chloro(trinonyl)silane, chloro(tridodecyl)silane, chloro(tritetradodecyl)silane, tris(chloromethyl)chlorosilane, tris(2-chloroethyl)chlorosilane, tris(3-chloropropyl)chlorosilane, tris(4-chlorobutyl)chlorosilane, (tricyclohexyl)chlorosilane, tris(3-methylcyclohexyl)chlorosilane, tris(3-chlorocyclohexyl)chlorosilane, chloro(triphenyl)silane, tris(3-chlorophenyl)chlorosilane, chloro(trinaphthyl)silane, chloro(tri)silane, chloro(tri)silane, chloro(tri)silane, chloro(tri)silane, chloro(diethyl)methylsilane, chloro(methyl)dipropylsilane, chloro(dibutyl)methylsilane, chloro(methyl)dipentylsilane, chloro(methyl)dioctylsilane, chloro(ditetradodecyl)methylsilane, chloro(bis-chloromethyl)methylsilane, chloro(bis-2-chloroethyl)methylsilane, chloro(bis-3-chloropropyl)methylsilane, chloro(bis-4-chlorobutyl)methylsilane, chloro(cyclohexyl)methylsilane, chloro(bis-3-chlorocyclohexyl)methylsilane, chloro(diphenyl)methylsilane, chloro(dinaphthyl)methylsilane, chloro(dixylyl)methylsilane chloro(di-m-chlorophenyl)methylsilane, chloro(bis-4-chloronaphthyl)methylsilane, chloro(dichlorotolyl)methylsilane, chloro(dichloroxylyl)methylsilane.

In one embodiment, the catalyst is the heterogeneous catalyst and the crude reaction product comprises less than 50 ppm $BCl_3$ or $AlCl_3$; alternatively the crude reaction product no detectable amounts of $BCl_3$ or $AlCl_3$; alternatively, the method includes the proviso that if the catalyst is a heterogeneous catalyst, then no $BCl_3$ or $AlCl_3$ are added in the method, alternatively less than 50 ppm $BCl_3$ or $AlCl_3$ are reacted in the method. $BCl_3$ and $AlCl_3$ are to be avoided in the method of the invention in embodiments where a heterogeneous catalyst are used since $BCl_3$ and $AlCl_3$ are harder to remove from the crude reaction product and may catalyze the formation of byproducts in later processing. This issue diminishes a benefit of using the heterogeneous catalyst, which is easy separation of the catalyst before subsequent processing steps.

The method of the invention may produce organohalosilanes in better yields, with better selectivity, and at lower temperature than with previously processes using known soluble catalysts and processes where only one hydridohalosilane is reacted. Furthermore, the heterogeneous catalyst of the method can be easily separated from crude product thereby decreasing catalysis of unwanted reactions during additional processing, such as product recovery by distillation, and increasing product purity.

The organosilane products of the present method are used as precursors to make many different commercial products including arylsiloxanes which have many commercial uses.

EXAMPLES

The invention is further illustrated by, and an invention embodiment may include any combinations of features and limitations of, the non-limiting examples thereof that follow.

The following examples are presented to better illustrate the method of the present invention, but are not to be considered as limiting the invention, which is delineated in the appended claims. Unless otherwise noted, all parts and percentages reported in the examples are by weight. The following table describes the abbreviations used in the examples:

TABLE 2

List of abbreviations used in the examples.

| Abbreviation | Word |
|---|---|
| G or g or gr. | gram |
| Me or me | methyl |
| Wt. | weight |
| mm | millimeter |
| % | percent |
| Mol | mole |
| Hr | hour |

TABLE 2-continued

List of abbreviations used in the examples.

| Abbreviation | Word |
|---|---|
| α | alpha |
| γ | gamma |
| ° C. | degrees Celsius |
| NA | Not Applicable |
| mL | milliliters |
| cm | Centimeter |
| w/w | Weight/weight; means that the percent is weight percent |
| " | Inch (with 1" = 2.54 centimeters) |
| CS331-3 | ⅛" extrusion, 200-300 m$^2$/g, γ-Alumina from Sud-Chemie Inc. |
| CS331-4 | ⅛" extrusion, 175-275 m$^2$/g, γ-Alumina from Sud-Chemie Inc. |
| CS331-5 | 1/10" CDS extrusion, 200-300 m$^2$/g, γ-Alumina from Sud-Chemie Inc. |
| Boria | $B_2O_3$ |
| Alumina | $Al_2O_3$—unless specified, refers to γ-alumina |
| Zirconium Oxide | $ZrO_2$ |
| XZO 1501/23 | High Porosity zirconium oxide calcined at 500° C. from MEL Chemicals |

Example of Method of Creating Alumina/Boria Catalyst 1.91 gr. $H_3BO_3$ (pre-ground with a mortar and pestle) was added to a porcelain dish along with 6.83 gr. of glycerol and stirred with a spatula until a consistent paste was obtained (5-10 minutes). 65.63 gr. $Al(NO_3)_3.9H_2O$ (pre-ground with a mortar and pestle) was then added and the mixture stirred for a couple of minutes. 4.08 gr. of de-ionized water was added and stirred until a consistent paste was obtained. The dish was then heated on a hotplate and heated to 90° C., at which point yellow vapors (nitrates) were observed. Heating was continued for 2 hours to drive off water as well as nitrates. The dish was then placed in an air circulating oven at 150° C. for 2 hours. When removed from the oven the material was a yellow, puffy, solid. The dish was then placed in an air circulating oven at 400° C. overnight. The resulting catalyst was 15% (w/w) boria and 85% (w/w) alumina. The other catalysts comprising alumina and boria were prepared using the same method except the amount of reagents were varied to provide the percentages of boria and alumina described in the examples.

Analysis by GC

Analysis was conducted using HP5890 and HP6890 gas chromatographs (GC's) equipped with a TCD detector and a 30 meter DB-210 column with an internal diameter of 0.25 mm and a film thickness of 0.50 μm.

Catalyst and Reactant Preparation Prior to Use in the Examples:

All reactant mixtures were prepared in a $N_2$ purged glovebag. Catalyst samples were prepared by drying in flowing $N_2$ at 300-400° C. overnight. The catalyst samples were transferred while still warm and under $N_2$ purge to vials and sealed. The vials containing catalyst were then transferred to a desiccator in a $N_2$ purged glovebag. Prior to use the vials for transferring catalyst were dried in an air circulated oven at 150° C. overnight and removed from the oven just prior to use.

Experimental Procedure Used in Examples

Catalysts and reactant mixtures were loaded into glass tubes, sealed on one end in a $N_2$ purged glovebag and temporarily sealed using a rubber setpa. The tubes comprised 1% (w/w) of catalyst if liquid, based on the weight of catalyst and reactants, and a consistent visual amount (approximately 1% (w/w) based on the weight of the catalyst and reactants) if solid. The loaded tubes, sealed with rubber septa's were then removed from the glovebag and sealed with a glass torch on the open end, below the rubber stopper. The sealed glass tubes containing reactant and catalyst were then heated in a metal heating block at a given temperature and time to carry out the reaction. Once removed from the heating block the tubes were cooled first at room temperature and then in a dry-ice/acetone bath. While cold the tubes were cracked open and temporarily sealed with a rubber septa until the reaction mixture was completely thawed. Once thawed, the reaction products were transferred from the glass tube reactor to a vial for analysis.

Example 1

A mixture containing a 2:1 molar ratio of benzene to methyldichlorosilane was placed in a series of glass tubes, each with CS331-4 alumina catalyst, and the tubes sealed. The tubes were heated to 275° C., at an estimated internal pressure of 1500 psi, for the times given in Table 1 below. At the indicated time, the tubes were cooled and the contents analyzed by GC-TCD. The results are presented as percent area under the curve, as defined by GC-TCD analysis.

TABLE 1

CS331-4 Alumina Catalyzed Reaction of Benzene with Methyldichlorosilane and Dichlorosilane.

| Time | GC-TCD Area Percent | | | | | |
|---|---|---|---|---|---|---|
| Min. | H2SiCl2 | MeHSiCl2 | MeSiCl3 | Benzene | PhMeSiCl2 | Ph2SiCl2 |
| 0 | 4.17 | 38.62 | 0.00 | 56.95 | 0.00 | 0.00 |
| 60 | 0.19 | 17.15 | 10.02 | 62.00 | 5.41 | 0.05 |
| 90 | 0.15 | 17.04 | 10.88 | 61.14 | 5.86 | 0.11 |
| 120 | 0.44 | 11.85 | 13.18 | 59.52 | 8.06 | 0.49 |
| 180 | 0.45 | 8.91 | 13.11 | 61.04 | 8.41 | 0.93 |
| 240 | 0.00 | 8.02 | 14.27 | 58.21 | 9.50 | 1.47 |

Example 2

A mixture containing a 2:1 molar ratio of benzene to methyldichlorosilane was placed in a series of glass tubes, each with CS331-5 alumina catalyst, and the tubes sealed. The tubes were heated to 175° C., at an estimated internal pressure of 1500 psi, for the times given in Table 2 below. At the indicated time, the tubes were cooled and the contents analyzed by GC-TCD. The results are presented as percent area under the curve, as defined by GC-TCD analysis.

TABLE 2

CS331-5 Alumina Catalyzed Reaction of Benzene with Methyldichlorosilane and Dichlorosilane

| Time | GC-TCD Area Percent | | | | | |
|---|---|---|---|---|---|---|
| Min. | H2SiCl2 | MeHSiCl2 | MeSiCl3 | Benzene | PhMeSiCl2 | Ph2SiCl2 |
| 0 | 4.17 | 38.62 | 0.00 | 56.95 | 0.00 | 0.00 |
| 60 | 0.95 | 34.24 | 0.27 | 55.72 | 3.98 | 0.10 |
| 120 | 0.43 | 32.43 | 0.45 | 53.83 | 6.79 | 0.19 |
| 180 | 0.74 | 29.99 | 0.69 | 52.95 | 9.73 | 0.29 |
| 240 | 0.72 | 29.86 | 0.70 | 53.17 | 9.60 | 0.28 |

Example 3

A mixture containing a 2:1 molar ratio of benzene to methyldichlorosilane was placed in a series of glass tubes, each with high porosity zirconium oxide (XZO1501/23) catalyst, and the tubes sealed. The tubes were heated to 250° C., at an estimated internal pressure of 1500 psi, for the times given in Table 3 below. At the indicated time, the tubes were cooled and the contents analyzed by GC-TCD. The results are presented as percent area under the curve, as defined by GC-TCD analysis.

TABLE 3

Zirconium Oxide (High Porosity) Catalyzed Reaction of Benzene with Methyldichlorosilane and Dichlorosilane

| Time | GC-TCD Area Percent | | | | | |
|---|---|---|---|---|---|---|
| Min. | H2SiCl2 | MeHSiCl2 | MeSiCl3 | Benzene | PhMeSiCl2 | Ph2SiCl2 |
| 0 | 4.17 | 38.62 | 0.00 | 56.95 | 0.00 | 0.00 |
| 60 | 2.78 | 28.92 | 1.32 | 61.15 | 1.00 | 0.00 |
| 120 | 0.00 | 23.16 | 3.38 | 60.13 | 4.23 | 0.00 |
| 180 | 2.82 | 18.25 | 6.38 | 56.68 | 7.66 | 0.00 |
| 240 | 0.00 | 16.61 | 6.94 | 53.97 | 10.80 | 0.00 |

Example 4

Samples of gamma-alumina were used as catalyst in the reaction of benzene and MeHSiCl$_2$ in glass tubes. Reactions were conducted using a 2:1 molar ratio of benzene to MeHSiCl$_2$ at 250° C. for 16 hours. The catalyst used in the reactions varied with respect to the treatment of the catalyst prior to the reaction. Two catalyst samples were dried without acid treatment and two samples were dried with acid treatment. The metal oxide catalyst samples were dried with no acid treatment were dried overnight (~16 hours) in flowing He at 300-325° C. The metal oxide catalyst dried with acid treatment were dried first in a flowing 50/50 mixture of He and anhydrous HCl for 4-5 hours at 300-325° C. and then overnight (~16 hours) in flowing He at 300-325° C. The reaction results with the two treatment methods are in Table 22 below. All reaction parameters were the same except for the catalyst treatment prior to use as the catalyst in the reaction. The results demonstrate the improved yield of PhMeSiCl$_2$ with catalyst acid treatment combined with drying compared to drying alone prior to using as catalyst in the reaction of benzene and MeHSiCl$_2$.

TABLE 4

The results are shown in the table below.

| Catalyst | PhMeSiCl$_2$ Yield % |
|---|---|
| CS331-3 | 8.63 |
| CS331-3 Acid Treated | 9.62 |
| CS331-4 | 7.48 |
| CS331-4 Acid Treated | 10.54 |

Comparative Example 1

A mixture containing a 2:1 molar ratio of benzene to methyldichlorosilane was placed in a series of glass tubes, each with a high porosity zirconium oxide (XZO1501/23) catalyst, and the tubes sealed. The tubes were heated to 250° C., at an estimated internal pressure of 1500 psi, for the times given in Table CE1. At the indicated time, the tubes were cooled and the contents analyzed by GC-TCD. The results are presented as percent area under the curve, as defined by GC-TCD analysis.

TABLE CE1

Zirconium Oxide (High Porosity) Catalyzed Reaction of Benzene with Methyldichlorosilane

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 32.00 | 0.81 | 64.53 | 0.15 |
| 90 | 27.87 | 2.05 | 63.94 | 2.18 |
| 120 | 26.63 | 2.35 | 63.38 | 2.87 |
| 180 | 20.92 | 4.50 | 59.72 | 7.57 |
| 240 | 18.44 | 5.32 | 60.02 | 8.69 |

Comparative Example 2

A mixture containing a 2:1 molar ratio of benzene to methyldichlorosilane was placed in a series of glass tubes, each with CS331-4 alumina catalyst, and the tubes sealed. The tubes were heated to 250° C., at an estimated internal pressure of 1500 psi, for the times given in Table CE2. At the indicated time, the tubes were cooled and the contents analyzed by GC-TCD. The results are presented as percent area under the curve, as defined by GC-TCD analysis.

TABLE CE2

CS331-4 Alumina Catalyzed Reaction of Benzene with Methyldichlorosilane.

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 23.95 | 6.57 | 62.65 | 2.06 |
| 90 | 18.94 | 9.52 | 61.90 | 3.73 |
| 120 | 17.90 | 10.22 | 61.33 | 3.99 |
| 180 | 14.35 | 11.78 | 60.71 | 5.36 |
| 240 | 11.23 | 12.76 | 60.67 | 6.64 |

Comparative Example 3

A mixture containing a 2:1 molar ratio of benzene to methyldichlorosilane was placed in a series of glass tubes, each with CS331-5 alumina catalyst, and the tubes sealed. The tubes were heated to 250° C., at an estimated internal pressure of 1500 psi, for the times given in Table CE3. At the indicated time, the tubes were cooled and the contents analyzed by GC-TCD. The results are presented as percent area under the curve, as defined by GC-TCD analysis.

TABLE CE3

CS331-5 Alumina Catalyzed Reaction of Benzene with Methyldichlorosilane.

| Time | GC-TCD Area Percent | | | |
|---|---|---|---|---|
| Min. | MeHSiCl2 | MeSiCl3 | Benzene | PhMeSiCl2 |
| 0 | 36.93 | 0.00 | 60.65 | 0.00 |
| 60 | 34.24 | 0.27 | 55.72 | 3.98 |
| 120 | 32.43 | 0.45 | 53.83 | 6.79 |
| 180 | 29.99 | 0.69 | 52.95 | 9.73 |
| 240 | 29.86 | 0.70 | 53.17 | 9.60 |

That which is claimed is:

1. A method for producing an organohalosilane, the method comprising:
reacting an organic compound comprising a halogen-substituted or unsubstituted aromatic compound with a hydridohalosilane mixture comprising at least two different hydridohalosilanes of formula (I) $R_n SiH_m X_{4-m-n}$, where each R is independently $C_1$-$C_{14}$ hydrocarbyl or $C_1$-$C_{14}$ hologen-substituted hydrocarbyl, X is fluoro, chloro, bromo, or iodo, n is 0, 1, or 2, m is 1, 2, or 3 and m+n is 1, 2, or 3, in the presence of a catalyst comprising one or more of the elements Sc, Y, Ti, Zr, Hf, Nb, B, Al, Ga, In, C, Si, Ge, Sn, or Pb, at a temperature greater than 100° C., and at a pressure of at least 690 kPa, to produce a crude reaction product comprising the organohalosilane,
provided that when the at least two different hydridohalosilane comprise a hydridohalosilane of formula (I) where n=0 and m=1 and a hydridohalosilane of formula (I) where n=0 and m=2, the catalyst is a heterogeneous catalyst comprising an oxide of one or more of the elements Sc, Y, Ti, Zr, Hf, B, Al, Ga, In, C, Si, Ge, Sn, or Pb.

2. The method as in claim 1, wherein the catalyst is the heterogeneous catalyst.

3. The method of claim 2, wherein the heterogeneous catalyst comprises alumina, zirconium dioxide, or an oxide of two or more of the elements Sc, Y, Ti, Zr, Hf, B, Al, Ga, In, C, Si, Ge, Sn, or Pb.

4. The method as in claim 3, wherein the heterogeneous catalyst comprises γ-alumina, a composite oxide comprising Al and one of the elements B, Zr, Ti, or Si, or a composite oxide comprising Zr and one of the elements B, Ti, or Si.

5. The method as in claim 4, wherein the heterogeneous catalyst comprises γ-alumina, a composite oxide comprising Zr and B, or a composite oxide comprising Al and B.

6. The method of claim 1, wherein the catalyst has the formula $Al_9B_2O_{15}$ or $Al_4B_2O_9$.

7. The method of claim 1, wherein the catalyst is the heterogeneous catalyst and the heterogeneous catalyst is treated with acid prior to the reacting.

8. The method of claim 1, wherein the catalyst has the formula $B_a Z_b$, $NbZ_5$, or $AlZ_3$, where Z is H, Cl, alkyl, or aryl, a is 1 or 2, and b is 3 or 6.

9. The method of claim 8, wherein the catalyst has the formula $PhBCl_2$, $BPh_3$, $B_2H_6$, $BCl_3$, $NbCl_5$, or $AlCl_3$.

10. The method of claim 9, wherein the catalyst has the formula $BCl_3$, $NbCl_5$, or $AlCl_3$.

11. The method as in claim 1, wherein the organohalosilane is of the formula $R'_e R_f SiH_g X_{4-e-f-g}$, wherein each R' is independently $C_1$-$C_{14}$ substituted or unsubstituted aryl or alkaryl, e is 1 or 2, f is 0, 1, or 2, g is 0, 1 or 2, and e+f+g=1, 2 or 3.

12. The method as in claim 1, wherein the organic compound comprises benzene, toluene, halobenzene, dihalobenzene, or naphthalene.

13. The method as in claim 1, wherein the organic compound is benzene.

14. The method as in claim 1, wherein m is 0 and n is 1 or 2 for one of the at least two hydridohalosilanes.

15. The method as in claim 1, wherein m=0 and n=1, 2, or 3 for one of the at least two hydridohalosilanes.

16. The method as in claim 1, wherein the hydridohalosilane mixture comprises dichloro(methyl)silane and dichlorosilane.

* * * * *